United States Patent [19]

Connor et al.

[11] Patent Number: 4,562,006

[45] Date of Patent: Dec. 31, 1985

[54] CYCLOHEPTADIENE DERIVATIVES

[75] Inventors: David T. Connor; Roderick J. Sorenson, both of Ann Arbor, Mich.

[73] Assignee: Warner-Lambert Company, Morris Plains, N.J.

[21] Appl. No.: 569,814

[22] Filed: Jan. 11, 1984

[51] Int. Cl.$^4$ .................... C07C 57/03; A61K 31/215; C11C 3/02

[52] U.S. Cl. ................................ 260/410; 260/501.1; 260/501.15; 514/529; 560/125; 560/128; 562/506; 562/510; 260/410.9 N; 260/413

[58] Field of Search ............................. 562/506, 510; 260/413 N, 413 L, 410.9 R, 410.9 D, 410.9 M, 501.1, 501.15; 560/125, 128; 514/529

[56] References Cited

U.S. PATENT DOCUMENTS

| | | | |
|---|---|---|---|
| 4,294,978 | 10/1981 | Sih | 562/503 |
| 4,432,906 | 2/1984 | Cohen et al. | 260/410.9 R |
| 4,434,101 | 2/1984 | Cohen et al. | 260/410.9 R |
| 4,442,099 | 4/1984 | Nicolaou et al. | 424/248.57 |

OTHER PUBLICATIONS

Urban et al., *The Canadian Journal of Microbiology* 1981, vol. 27, No. 12, p. 1283.
*The Merck Index of Chemicals and Drugs*, 7th Edition, 1960 by Merck and Co., Inc., p. 594.

*Primary Examiner*—James H. Reamer
*Assistant Examiner*—John T. Sullivan
*Attorney, Agent, or Firm*—Joan Thierstein

[57] ABSTRACT

Cycloheptadiene analogues of arachidonic acid as well as their cyclopropyl intermediates are described as inhibiting human leukocyte lipoxygenase and antagonizing SRS-A. Methods of manufacture and pharmaceutical compositions are described. The compounds are useful in treating allergic diseases, cardiovascular diseases and immunoinflammatory diseases.

12 Claims, No Drawings

CYCLOHEPTADIENE DERIVATIVES

BACKGROUND OF THE INVENTION

Arachidonic acid serves as the biological precursor of a growing family of physiologically active eicosanoids which include cyclooxygenase derived products such as prostaglandins-E's and F's, thromboxanes, prostacyclin, and lipoxygenase-derived products such as hydroperoxy- and hydroxy-eicosatetraenoic acids (HPETE and HETE) and leukotrienes.

Recently, lipoxygenase pathway products such as leukotrienes-$B_4$, $C_4$, and $D_4$, 5-HPETE; 5-HETE and 12-HETE have been implicated in inflammation and in allergic and immune responses. These lipoxygenase products have been shown to be highly potent, stereospecific inducers of polymorphonuclear leukocyte migration or chemotaxis, lysosomal enzyme release and degranulation, as well as contraction of smooth muscles such as vascular and pulmonary tissue, and induce the generation of additional inflammogens such as thromboxane $A_2$ and prostacyclin. Lipoxygenase products also interact with vasodilator prostanoids and other mediators which leads to an enhancement or amplification of the inflammatory response.

Leukotrienes and HETES play a major role in the pathogenesis of many conditions. They have been found in synovial fluid of rheumatoid joints, in involved skin of psoriatic patients, in inflamed colonic tissue, and elevated in ischemic myocardial tissue. They are major mediators of allergic and asthmatic conditions as well.

Lipoxygenase inhibitors or leukotriene biosynthesis inhibitors will thus be useful in treating a number of diseases whose pathogenesis involves production of leukotrienes and other lipoxygenase derived products and subsequent tissue damage or inflammation due to infiltration of leukocytes, release of digestive lysosomal enzymes, changes in permeability, and contractile state of smooth muscle tissue. Conditions in which such inhibitors would be useful include allergy, asthma, arthritis, psoriasis, inflammation, inflammatory bowel diseases, pain, and cardiovascular disorder such as myocardial ischemia and infarction, stroke, and atherosclerosis.

SUMMARY OF THE INVENTION

The present invention relates to compounds of the formula

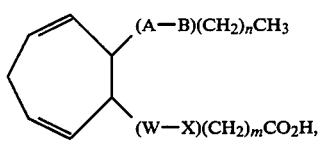

(A—B)(CH$_2$)$_n$CH$_3$ (W—X)(CH$_2$)$_m$CO$_2$H,   I

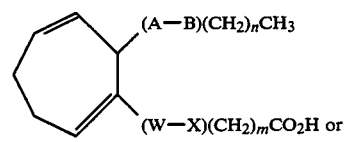

(A—B)(CH$_2$)$_n$CH$_3$ (W—X)(CH$_2$)$_m$CO$_2$H or   II

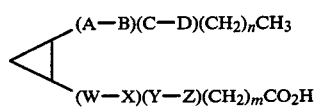

(A—B)(C—D)(CH$_2$)$_n$CH$_3$   III (W—X)(Y—Z)(CH$_2$)$_m$CO$_2$H in which (A-B), (C-D), (W-X), (Y-Z) are each independently (CH$_2$)$_2$,

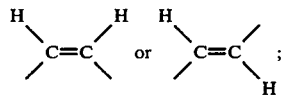

n and m are each independently one to ten; esters and pharmaceutically acceptable base salts thereof.

The present invention includes methods of manufacture, pharmaceutical compositions comprising an effective amount of a compound of the formula I, II, or III with a pharmaceutically acceptable carrier, as well as a method of treatment of asthma and other allergic diseases, arthritis and other immunoinflammatory diseases, cardiovascular diseases, psoriasis, and cancer by administering an effective amount of a compound of the formula I, II, or III in unit dosage form.

DETAILED DESCRIPTION

Esters of the carboxylic acids of the formulae I, II, and III are alkyl, alkenyl, aryl, or arylalkyl esters. Alkyl esters are especially lower alkyl esters of one to six carbon atoms in a straight or branched hydrocarbon chain such as, for example, methyl, ethyl, n-propyl, isopropyl, butyl, isobutyl, sec-butyl, tert-butyl, and the like.

Aryl esters are especially those containing a phenyl or phenyl group substituted by halogen, e.g., fluorine, chlorine, or bromine, lower alkyl of one to four carbon atoms, lower alkoxy of one to four carbon atoms, hydroxy or trifluoromethyl.

Arlalkyl esters are especially those containing an aryl group as defined above, i.e., phenyl or substituted phenyl bonded to a lower alkyl hydrocarbon chain of one to four carbon atoms. Examples of such groups are benzyl and substituted benzyl, phenethyl and substituted phenethyl and the like.

The above defined esters of the carboxylic acids of the formula I, II, and III may be prepared by standard methods known in the art, for example by treating the appropriate acid and alcohol in the presence of an acid.

Pharmaceutically acceptable base salts are those derived from inorganic bases such as lithium hydroxide, sodium hydroxide, potassium hydroxide or ammonium hydroxide, or organic bases such as triethylamine, arginine, N-methylglucamine, and the like. These salts may be prepared by standard methods known in the art.

Preferred embodiments of the present invention are the compounds of formulae I, II, and III wherein n is 4 and m is 3.

Particularly preferred embodiments of the present invention are:

6-(7-heptyl-2,5-cycloheptadien-1-yl)-5-hexenoic acid.

7-(1-heptenyl)-2,5-cycloheptadiene-1-hexanoic acid (Z).

7-(1-heptenyl)-2,5-cycloheptadiene-1-butanoic acid (Z).

6-[7-(1-heptenyl)-1,5-cycloheptadiene-1-yl]-5-hexenoic acid.

8-[2-(1,3-nonadienyl)cyclopropyl]-7-octenoic acid (Z,E,Z).

6-[2-(1,3-nonadienyl)cyclopropyl]-5-hexenoic acid (Z,E,Z).

8-[2-(1-nonenyl)-1-cyclopropyl]-7-octenoic acid, lithium salt (Z,Z).

8-[2-(1-nonenyl)-1-cyclopropyl]-5,7-octadienoic acid (Z,E,Z).

The compounds of the present invention may be prepared by reacting an appropriate aldehyde of the formula (W-X) is

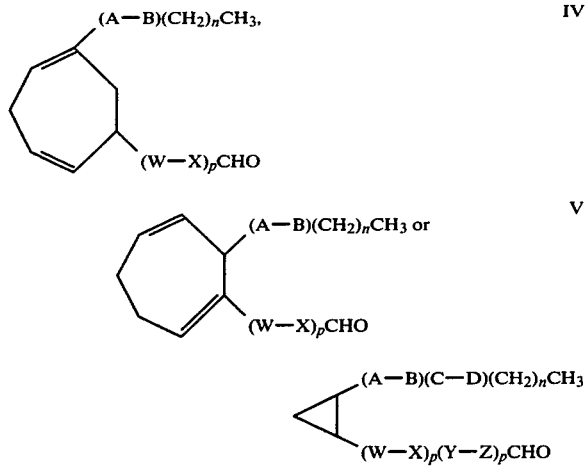

wherein (A-B) is as defined above;

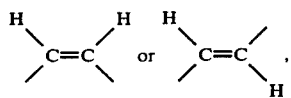

and p is 0 or 1, with a compound of the formula

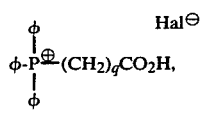

an ester or base salt thereof, wherein φ stands for phenyl, Hal stands for halide, especially bromide, and q is an integer of from 2 to 13, in the presence of a base.

The above reaction is preferably carried out at or near room temperature, i.e., from about 20° to 30° C. in an inert solvent or solvent mixture such as tetrahydrofuran, diethylether, dimethylformamide, dimethylsulfoxide, or a mixture of the ether solvent with dimethylformamide or dimethylsulfoxide. The reaction is also carried out in the presence of a base such as, for example, an alkyl lithium or, preferably sodium hexamethyldisilazide.

Compounds of the formula I may also be prepared by a thermal rearrangement reaction where certain compounds of formula III, in which (A-B), (W-X) are each independently

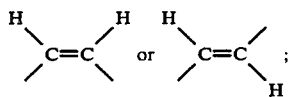

are heated in a sealed tube at elevated temperatures, preferably between about 175° and about 210° C., and if desired, converting the resulting free acids to corresponding esters or salts thereof.

Compounds of the formula III where in (W-X) is

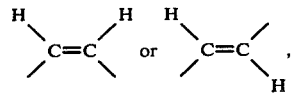

are thus also useful as intermediates.

Starting materials for the above reactions are known and/or, if new, may be prepared according to known methods.

The compounds in the present invention exhibit significant inhibition of human leukocyte lipoxygenase and antagonize SRS-A. They have the potential to inhibit various other enzymes in the arachidonic acid cascade and to antagonize the effects of various biologically active substances produced in the arachidonic acid cascade pathways.

The details of the human leukocyte lipoxygenase assay are described below. The soybean lipoxygenase radiochemical is described in *Prostaglandins, Leukotrienes, and Medicine*, 11, 373–80 (1983). The leukotriene receptor binding assay is described by R. F. Bruns, W. J. Thomsen, and T. A. Pugsley in *Life Sciences*, 33, 645 (1983).

Human Leukocyte and Platelet Lipoxygenase Assay

An acetone-pentane powder of leukocyte and platelets was prepared from buffy coat obtained from the Michigan Red Cross and Michigan Department of Health in Lansing, Michigan, and was suspended in 5-7 volumes of cold 0.1M tris buffer, pH 7.4 containing 0.154 M NaCl. The suspension was centrifuged at 13,300 g for ten minutes at 4° C. The resultant pellet was retained, resuspended in five volumes of cold acetone, recentrifuged at 13,300 g and resuspended in five volumes of cold pentane. The pentane suspension was centrifuged for ten minutes at 13,300 g to give a pellet which was dried in the cold under vacuum with periodic pulverization. The dry powder is stable for several weeks when stored at −80° C.

Enzyme Stock Solution

This was prepared in the following manner. About 15 mg of the acetone-pentane powder is suspended in 4 ml of cold tris buffer (0.1M, pH 7.4), allowed to stand for five minutes and homogenized thoroughly. The homogenate is sonicated three times for 15 seconds each time, diluted to 7 ml with cold tris buffer (0.1M, pH 7.4) and centrifuged at 4° for 60 minutes at 13,300 g. The supernatant is retained and diluted to a total of 10 ml with cold tris buffer (0.1M, pH 7.4) to give the stock enzyme solution. Additional dilutions 2–50 fold are done as necessary to locate optimal enzyme reaction rate in the assay described below.

Substrate

This solution is prepared at 100 μM or 1.0 μM concentrations of arachidonic acid or linoleic acid in 0.1 M tris buffer, pH 9.0 containing 20% ethanol.

Human Leukocyte and Platelet Lipoxygenase Assay

The enzyme reaction is followed spectrophotometrically by the appearance of a conjugated diene product at 234 nm. The reaction is monitored at 24° using a Gilford Model 2500 spectrophotometer. Each assay had a total volume of 1.0 ml and contained arachiodonic acid at 10 μM, tris buffer (0.1M, pH 9.0), 2% ethanol and sufficient enzyme to give an easily measurable initial rate of reaction. The effects of inhibitors on the reaction were compared with control reactions run under identical conditions. Routinely, inhibitors were incubated with the enzyme for five minutes prior to addition of substrate to initiate the reaction.

Inhibitors were also studied in the presence of 10 $\mu$M indomethacin. In this case each assay contained a total volume of 1.0 ml and had arachiodonic acid at 0.1 $\mu$M, tris buffer (0.1M, pH 9.0), 10 $\mu$M of indomethacin, 2% ethanol, and sufficient enzyme to give an easily measurable initial reaction rate.

The following tables illustrate the activity of certain representative compounds of the present invention. The RBL-1 column represent data from the leukotriene receptor binding assay and the LDA(U) column reports on the human leukoxyte lipoxygenase assay.

TABLE 1

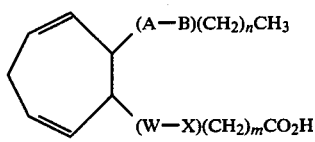

| Ex. No. | (A—B) | (W—X) | n | m | IC$_{50}$ ($\mu$M) RBL-1 | LDA($\mu$) |
|---|---|---|---|---|---|---|
| 12 | H\C=C/H | CH$_2$CH$_2$ | 4 | 3 | 26.36 | 0.74 |
| 14 | H\C=C/H | CH$_2$CH$_2$ | 4 | 1 | 53.38 | |
| 6 | CH$_2$CH$_2$ | H\C=C/H | 4 | 3 | 23.93 | |

TABLE 2

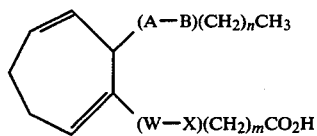

| Ex. No. | (A—B) | (W—X) | n | m | IC$_{50}$ ($\mu$M) RBL-1 | LDA($\mu$) |
|---|---|---|---|---|---|---|
| 18 | H\C=C/H | H\C=C/H | 4 | 3 | 17.08 | |

TABLE 3

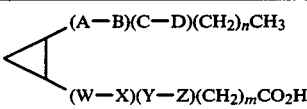

| Ex. No. | (A—B) | (C—D) | (W—X) | (Y—Z) | n | m | IC$_{50}$ ($\mu$M) RBL-1 | LDA($\mu$) |
|---|---|---|---|---|---|---|---|---|
| 11 | H\C=C/H (H down) | H\C=C/H | H\C=C/H | CH$_2$CH$_2$ | 4 | 3 | 10.34 | |
| 13 | H\C=C/H (H down) | H\C=C/H | H\C=C/H | CH$_2$CH$_2$ | 4 | 1 | 26.41 | |

In view of the above activity, the compounds of this invention, including nontoxic salts, are indicated in the management of asthma and other allergic diseases, arthritis and other immunoinflammatory diseases, cardiovascular diseases, psoriasis, and cancer. The compounds may also have sleep inducing, wound healing, and transplant rejection properties. These compounds will be generally useful for the treatment of any disease which benefits from modulation of the arachidonic acid cascade.

The present invention thus includes compositions containing a compound of formula 1 in treating disease such as autoimmune disease characterized by abnormal immune response in warm-blooded animals. According to this aspect of the invention, the properties of the compounds of the invention are utilized by administering to a warm-blooded animal an effective amount of a pharmaceutical composition containing as the active ingredient at least about 0.1 percent by weight, based on the total weight of the composition of at least one such compound of the invention.

Pharmaceutical compositions of the invention can be formulated in any suitable way, preferably with an inert carrier for administration orally, parenterally, ophthalmically, topically, or by suppository.

For example, the compounds of the present invention are formulated into dosage forms such as tablets or syrups by blending with an inert pharmaceutical carrier such as lactose or simple syrup by methods well known in the art. For injectionable dosage forms, they are formulated with vehicles such as water, peanut oil, sesame oil, and the like. In these dosage forms, the active ingredient is from about 0.05 grams to 0.5 grams per dosage unit.

The present invention is further illustrated by way of the following examples.

EXAMPLE 1

Cyclopropanecarboxylic Acid, 2-(1-nonenyl), ethyl ester, (Z)

A mixture of dimethyl sulfoxide (150 ml), and sodium hydride (6.5 g, 0.271 moles) which has been washed with hexane under argon, is heated at 70° C. until gas evolution ceases and a dark green clear solution is obtained. The solution is cooled to room temperature and a solution of n-octyltriphenylphosphonium bromide (124 g, 0.272 moles) in dimethyl sulfoxide (200 ml) is added slowly. After 15 minutes a solution of ethyl 2-formylcyclopropane-1-carboxylate (38.7 g, 0.272 moles) in dimethyl sulfoxide (50 mls) is added and the resulting mixture is stirred at room temperature overnight. The mixture is poured into ice-water (1000 mls), stirred well, and extracted with ether (3×300 ml). The combined extracts are washed with aqueous sodium chloride solution and dried over magnesium sulfate. The solvent is removed at reduced pressure to give a semi-crystalline residue. The residue is triturated with petroleum ether and filtered. The solvent is stripped from the filtrate to give an oil (59 g). The oil is dissolved in a mixture of ether/petroleum ether and filtered through a column of silica gel. The solvents are removed to give an oil, which is distilled at reduced pressure to give the product, as a clear colorless oil (28 g, 43%), b.p. 86°-91° C. (0.05 mm).

EXAMPLE 2

Cyclopropanemethanol, 2-(1-nonenyl)-,(Z)-

A solution of cyclopropanecarboxylic acid, 2-(1-nonenyl), ethyl ester (29.5 g, 0.124 moles) in ether (100 ml) is added to a refluxing mixture of lithium aluminum hydride (5.4 g, 0.135 moles) in ether (250 ml) under nitrogen. The mixture is refluxed for 1.5 hours and then cooled. Water is added dropwise until gas evolution ceases. 3N sulfuric acid is added until a clear solution forms. The layers are separated and the aqueous layer is extracted with ether. The combined ether fractions are dried (magnesium sulfate) and evaporated to give the crude product (24.1 g, 99%). Distillation at reduced pressure gives the product as a clear colorless oil (21.6 g, 89%), b.p. 85°-88° (0.07 mm).

EXAMPLE 3

Cyclopropanecarboxaldehyde, 2-(1-nonenyl)-,(Z)-

A solution of cyclopropanemethanol, 2-(1-nonenyl)-, (21.6 g, 0.11 moles) in methylene chloride (25 ml) is added dropwise to a solution of pyridinium dichromate (79.8 g, 0.208 moles) in methylene chloride (200 ml) at room temperature under nitrogen. The reaction mixture is stirred overnight. The mixture is diluted with ether (500 ml), filtered through celite and then through a short column of silica gel. The solvents are stripped from the filtrate to give the crude product (21.6 g). Distillation at reduced pressure gives the product as a clear colorless oil (14.8 g, 69%), b.p. 81°-86° C. (0.06 mm).

EXAMPLE 4

2-Propanealdehyde, 3[2-(1-nonenyl)cyclopropyl]-,

A mixture of cyclopropanecarboxyaldehyde, 2-(1-nonenyl)-, (4.6 g, 0.024 moles), and formylmethylenetriphenylphosphorane (7.2 g, 0.024 moles) in tetrahydrofuran (50 ml) is refluxed under nitrogen for three days. The solvent is removed under reduced pressure. The residue is triturated with ether/hexane (1:1) and filtered. The solvent is stripped from the filtrate to give a dark oil. The oil is dissolved in ether/hexane (1:1) and filtered through column of silica gel. The filtrate is evaporated to give the crude product (2.4 g, 55%). Flash chromatography on silica gel (ether/petroleum ether 4:1) gives the product (1.8 g, 35%).

EXAMPLE 5

5,7-Octadienoic acid, 8-[2-(1-nonenyl)-1-cyclopropyl]-, (Z,E,Z)

Sodium hexamethyldisilazide (2.5 g, 0.0136 moles) is added to a stirred suspension of 4-carboxybutyltriphenylphosphonium bromide (3.0 g, 0.0068 moles) in tetrahydrofuran (25 ml) and dimethylformamide (5 ml) under nitrogen at room temperature. The mixture is stirred for 20 minutes and a solution of 2-propenaldehyde, 3-[2-(1-nonenyl)cyclopropyl-, (1.5 g, 0.0068 moles) is added. The resulting mixture is stirred for one hour at room temperature, diluted with water (50 ml) and extracted with ether (50 ml). The layers are separated and the organic layer is extracted with water (50 ml). The combined water layers are washed with ethyl acetate, acidified with 4N hydrochloric acid and extracted with ethyl acetate (3×50 ml). The ethyl acetate extracts are combined, washed with water and dried (magnesium sulfate). The solvent is evaporated to give a yellow oil (1.4 g, 68%). Flash chromatography on silica gel (ether/petroleum ether 3:7) gives the product as a yellow oil (0.8 g, 39%).

EXAMPLE 6

5-Hexenoic acid, 6-(7-heptyl-2,5-cycloheptadien-1-yl)-

5,7-octadienoic acid, 8-[2-(1-nonenyl)-1-cyclopropyl]-, (0.5 g, 0.0016 moles) is heated at 195°-200° C. for one hour in a sealed stainless steel bomb under argon. The product is washed out of the bomb with ether/petroleum ether. The resulting solution is filtered through a short silica gel column and evaporated to give a clear yellow oil (0.5 g, 100%).

EXAMPLE 7

Cyclopropanecarboxylic acid, 2-(2-formylethenyl)-ethyl ester

A mixture of ethyl 2-formyl-1-cyclopropanecarboxylate (55 g, 0.39 moles) and formylmethylenetriphenylphosphorane (117.7 g, 0.39 moles) in tetrahydrofuran (600 ml) is refluxed for 40 hours. The solvent is removed under reduced pressure. The residue is triturated with ether/hexane (1:1) and filtered. The filtrate is evaporated, dissolved in ether/petroleum ether and filtered through a column of silica gel. The solvent is stripped from the filtrate to give a dark oil. The oil is distilled under reduced pressure to give the product as a clear colorless oil (52.1 g, 80%), b.p. 105°-113° C. (2.0 mm).

EXAMPLE 8

Cyclopropanecarboxylic acid, 2-(1,3-nonadienyl)-, ethyl ester

A mixture of dimethyl sulfoxide (90 ml) and sodium hydride (4.75 g, 0.20 moles) which has been washed with hexane under argon, is heated at 70° C. until gas evolution ceases (about 90 minutes). The solution is cooled to room temperature and a solution of n-hexyltriphenylphosphonium bromide (84.2 g, 0.20 moles) in dimethyl sulfoxide (180 ml) is added slowly. After 15 minutes a solution of cyclopropanecarboxylic acid, 2-(2-formylethenyl)-ethyl ester (33.2 g, 0.20 moles) in dimethyl sulfoxide (40 ml) is added and the mixture is cooled with an ice-bath for 20 minutes. The reaction mixture is stirred at room temperature overnight. The mixture is diluted with water (600 ml) and then stirred vigorously with petroleum ether (600 ml). The precipitate is filtered and washed several times with petroleum ether. The layers of the filtrate are separated and the aqueous layer is extracted with petroleum ether (2×250 ml). The combined organic fractions are dried (magnesium sulfate) and evaporated to give a clear yellow oil (46.4 g, 97%). The oil is dissolved in ether/petroleum ether (3:7) and filtered through a short silica gel column. The solvent is stripped from the filtrate to give the product as a clear yellow oil (38 g, 81%).

EXAMPLE 9

Cyclopropanemethanol, 2-(1,3-nonadienyl)-, (E,Z)

A solution of cyclopropanecarboxylic acid, 2-(1,3-nonadienyl)-,ethyl ester (31.3 g, 0.132 moles) in ether (150 ml) is added to a refluxing mixture of lithium aluminum hydride (8.0 g, 0.2 moles) in ether (150 ml) under nitrogen. The mixture is refluxed for 1.5 hours and then cooled. Water is added dropwise until gas evolution ceases. 3N sulfuric acid is added until a clear solution forms. The layers are separated and the aqueous layer is extracted with ether. The combined ether fractions are washed with aqueous sodium chloride solution, dried over magnesium sulfate and evaporated to give a pale yellow oil (25.7 g). Distillation at reduced pressure gives the product as an oil (17.8 g, 70%), b.p. 98°–113° C. (0.3 to 0.25 mm).

EXAMPLE 10

Cyclopropanecarboxaldehyde, 2-(1,3-nonadienyl)-(E,Z)

A solution of cyclopropanemethanol, 2-(1,3-nonadienyl)-, (11.6 g, 0.06 moles) in methylene chloride (50 ml) is added to a stirred suspension of pyridinium dichromate (42.4 g, 0.119 moles) in methylene chloride (100 ml) at room temperature under argon. The reaction mixture is stirred at room temperature overnight. The reaction mixture is diluted with ether (300 ml), filtered through celite and then through a short column of silica gel. The solvents are stripped from the filtrate to give a yellow oil (9.4 g, 82%). Flash chromatography on silica gel (ether/petroleum ether, 3:7) gives the product as a colorless oil (4.6 g, 40%).

EXAMPLE 11

7-Octenoic acid, 8-[2-(1,3-nonadienyl)cyclopropyl]-, (Z,E,Z)

Sodium hexamethyldisilazide (3.0 g, 0.014 moles) is added to a stirred suspension of 6-carboxyhexyltriphenylphosphonium bromide (6.8 g, 0.014 moles) in tetrahydrofuran (50 ml) under nitrogen at room temperature for 20 minutes and then a solution of cyclopropanecarboxaldehyde, 2-(1,3-nonadienyl)-, (3.0 g, 0.014 moles) is added. The resulting mixture is stirred for one hour at room temperature, diluted with water (50 ml) and extracted with ether (50 ml). The layers are separated and the organic layer is extracted with water (50 ml). The combined aqueous layers are washed with ethyl acetate, acidified with 4N hydrochloric acid and extracted with ethyl acetate (3×50 ml). The combined ethyl acetate extracts are washed with water and dried (magnesium sulfate). The solvent is evaporated to give a dark brown syrup (3.7 g, 78%). Flash chromatography on silica gel (ether/petroleum ether 1:1) gives the product as a yellow oil (1.7 g, 36%).

EXAMPLE 12

2,5-Cycloheptadiene-1-hexanoic acid, 7-(1-heptenyl)-(Z)-

7-octenoic, 8-[2-(1,3-nonadienyl)cyclopropyl]-(0.9 g, 0.003 moles) is heated at 200° C. for one hour in a sealed stainless steel bomb under argon. The product is washed out of the bomb with ether/petroleum either to give an amber colored oil. Flash chromatography on silica gel (ether/petroleum ether 3:7) gives the product as a pale yellow oil (0.6 g, 66%).

EXAMPLE 13

5-hexenoic acid, 6-[1,3-nonadienyl)cyclopropyl]-, (Z,E,Z)

Prepared by the method described in Example 11 from cyclopropanecarboxaldehyde, (2-(1,3-nonadienyl)-, (2.9 g, 0.014 moles), and 4-carboxybutyltriphenylphosphonium bromide (6.9 g, 0.016 moles). Flash chromatography of the crude product (4.1 g, 98%) on silica gel (ethyl acetate) gives the pure product as an amber oil (2.5 g, 60%).

EXAMPLE 14

2,5-cycloheptadiene-1-butanoic acid, 7-(1-heptenyl)-, (Z)-

Prepared by the method described in Example 12 from 5-hexenoic acid, 6-[2-(1,3-nonadienyl)cyclopropyl]-(1.0 g, 0.0026 moles). Flash chromatography of the crude product on silica gel (ether/petroleum ether) gave the product as a yellow oil (0.6 g, 60%).

EXAMPLE 15

7-Octenoic acid, 8-[2-(1-nonenyl)-1-cyclopropyl)-, ethyl ester, (ZZ)-

Prepared by the method described in example 1 from cyclopropanecarboxaldehyde, 2-(1-nonenyl)-, (5.0 g, 0.026 moles), and 6-carbethoxyhexyltriphenylphosphonium bromide (12.94 g, 0.026 moles). Molecular distillation of the crude product gave an oil (1.4 g, 16%).

EXAMPLE 16

7-Octenoic acid, 8-[2-(1-nonenyl)-1-cyclopropyl]-, lithium salt

A mixture of 7-octenoic acid, 8-[2-(1-nonenyl)-1-cyclopropyl]-ethyl ester (0.5 g, 0.0015 moles) and 0.5N lithium hydroxide (12 ml) in tetrahydrofuran (10 ml) is stirred at room temperature for four days. The tetrahydrofuran is removed under reduced pressure. The product is filtered off, washed with water and dried. Recrystallization from ethanol gives the product as a white solid (0.15 g, 32%), m.p. 192° C. (decomposes).

EXAMPLE 17

1,5-Cycloheptadienecarboxaldehyde, 7-(1-heptenyl)-, (Z)

A mixture of cyclopropanecarboxaldehyde, 2-(1,3-nonadienyl)-, (4.0 g, 0.021 moles) and formylmethylenetriphenylphosphorane (6.35 g, 0.021 mole) in tetrahydrofuran (100 ml) is refluxed under argon for 140 hours. The solvent is evaporated under reduced pressure. The crystalline residue is triturated with hexane, filtered, and washed several times with hexane. The filtrate is evaporated to give an oily residue.

EXAMPLE 18

5-Hexenoic acid, 6-[7-(1-heptenyl)-1,5-cycloheptadien-1-yl]-

Sodium hexamethyldisilazide (2.9 g, 0.016 moles) is added to a stirred suspension of 4-carboxybutyltriphenylphosphonium bromide (3.45 g, 0.08 moles) in tetrahydrofuran (50 ml) and dimethylformamide (5 ml) under nitrogen at room temperature. The mixture is stirred for 20 minutes and a solution of 7-(1-heptenyl)-1,5-cycloheptadienecarboxaldehyde (1.7 g, 0.008 moles) is added. The resulting mixture is stirred for one hour at room temperature, diluted with water (50 ml) and extracted with ether (50 ml). The layers are separated and the organic layer is extracted with water (50 mls). The combined water layers are washed with ethyl acetate, acidified with 4N hydrochloric acid and extracted with ethyl acetate (3×50 ml). The ethyl acetate extracts are combined, washed with water and dried (magnesium sulfate). The solvent is evaporated to give yellow oil (2.3 g, 93%). Flash chromatography on silica gel (ether/petroleum ether, 4:6) gives the product as a clear yellow oil (0.9 g, 36%).

EXAMPLE 19

2-Propenaldehyde,3-[2-(1,3-nonadienyl)cyclopropyl], ethylene ketal

Sodium hexamethyldisilazide (5.1 g, 0.028 moles) is added to a stirred solution of (1,3-dioxolan-2-ylmethyl)-triphenylphosphonium bromide (12 g, 0.028 moles) in tetrahydrofuran (100 mls) under argon at room temperature. The mixture is stirred for 30 minutes and a solution of 2-(1,3-nonadienyl) cyclopropanecarboxaldehyde (5.4 g, 0.028 moles) in tetrahydrofuran (40 ml) is added dropwise. The resulting mixture is stirred overnight and poured into ice-water (250 ml). The tetrahydrofuran is removed at reduced pressure and the aqueous residue is extracted with ether (3×100 ml). The combined ether extracts are washed with aqueous sodium chloride solution, dried over magnesium sulfate and evaporated to give an orange oil (8.0 g). Chromatography on neutral alumina (ether/petroleum ether, 1:1) gives the product as a clear colorless oil (5.2 g, 71%).

EXAMPLE 20

2-Propenaldehyde, 3-[2-(1,3-nonadienyl)cyclopropyl]-

A few crystals of para-toluenesulfonic acid are added to a solution of 2-propenaldehyde, 3-[2-(1,3-nonadienyl)cyclopropyl], ethylene ketal (2.5 g, 0.01 moles) in acetone (20 ml) under argon and the mixture is stirred for 19 hours. The acetone is removed under vacuum. The residue is dissolved in ether and filtered through a short column of silica gel. The filtrate is evaporated to give a syrup (2.1 g). This syrup contains the product contaminated with unknown impurities. It is used for the next reaction without further purification.

EXAMPLE 21

2,5-Cycloheptadienecarboxyaldehyde, 7-(1-heptenyl)-ethylene ketal

Prepared by the method described in Example 12 from 2-propenaldehyde, 3-[2-(1,3-nonadienyl) cyclopropyl], ethylene ketal (1.0 g, 0.0028 moles). The product was obtained as an oil (1.0 g).

We claim:

1. A compound of the formula

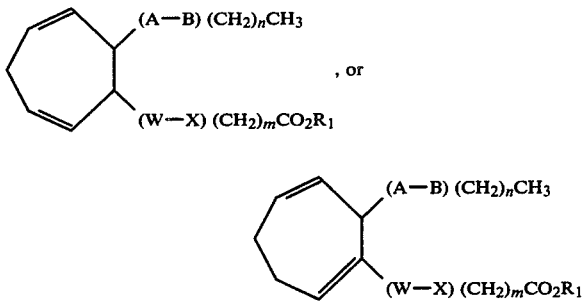

in which (A-B), (C-D), (W-X), and (Y-Z) are each independently $(CH_2)_2$,

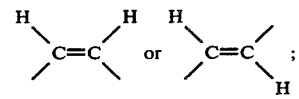

n and m are each independently integers one to ten; and $R_1$ is selected from hydrogen lower alkyl, lower alkenyl, phenyl, phenyl lower alkyl, and phenyl and phenyl lower alkyl substituted in the phenyl ring by halogen, lower alkyl, lower alkoxy, hydroxy, or trifluoromethyl, or a pharmaceutically acceptable base salt thereof.

2. A compound according to claim 1, wherein n is 4 and m is 3.

3. A compound according to claim 1 and being 6-(7-heptyl-2,5-cycloheptadien-1-yl)-5-hexenoic acid (Z).

4. A compound according to claim 1 and being 7-(1-heptenyl)-2,5-cycloheptadiene-1-hexanoic acid (Z).

5. A compound according to claim 1 and being 7-(1-heptenyl)-2,5-cycloheptadiene-1-butanoic acid (Z).

6. A compound according to claim 1 and being 6-[7-(1-heptenyl)-1,5-cycloheptadien-1-yl]-5-hexenoic acid (Z,Z).

7. A compound according to claim 1 and of the formula

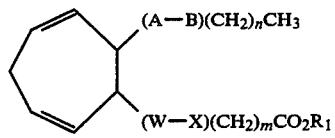

in which (A-B) and (W-X) are each independently

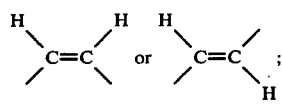

n and m are each independently one to ten, and $R_1$ is selected from hydrogen, lower alkyl, lower alkenyl, phenyl, phenyl lower alkyl, and phenyl and phenyl lower alkyl substituted in the phenyl ring by halogen, lower alkyl, lower alkoxy, hydroxy or trifluoromethyl or a pharmaceutically acceptable base salt thereof.

8. A compound according to claim 1 and of the formula

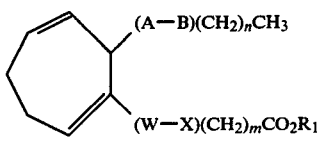

wherein (A-B) and (W-X) are each independently

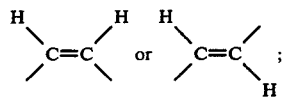

n and m are each independently integers one to ten; and $R_1$ is selected from hydrogen, lower alkyl, lower alkenyl, phenyl, phenyl lower alkyl, and phenyl and phenyl lower alkyl substituted in the phenyl ring by halogen, lower alkyl, lower alkoxy, hydroxy or trifluoromethyl or a pharmaceutically acceptable base salt thereof.

9. A pharmaceutical composition comprising an amount effective for modulating the arachidonic acid cascade of a compound according to claim 1 in admixture with a pharmaceutically acceptable carrier.

10. A method of treating diseases in a mammal which benefits from modulation of the arachidonic acid cascade comprising administering to said mammal a pharmaceutical composition according to claim 9.

11. A compound according to claim 7 wherein n is 4 and m is 3.

12. A compound according to claim 8 wherein n is 4 and m is 3.

* * * * *

UNITED STATES PATENT AND TRADEMARK OFFICE
CERTIFICATE OF CORRECTION

PATENT NO. : 4,562,006
DATED : 12/31/85
INVENTOR(S) : Connor, David T. & Sorenson, Roderick J.

It is certified that error appears in the above—identified patent and that said Letters Patent is hereby corrected as shown below:

Column 3, line 5, delete "(W-X is"
Column 3, lines 6-14 change formula IV
from (A-B)(CH$_2$)$_n$CH$_3$" to

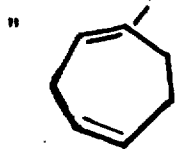

" 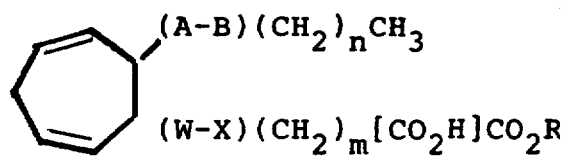

Column 3, line 26 after "above" add --W-X--.
Claim 1, column 12, line 30, delete "(C-D)" and "(Y-Z)"

Signed and Sealed this

Nineteenth Day of August 1986

[SEAL]

Attest:

DONALD J. QUIGG

Attesting Officer  Commissioner of Patents and Trademarks